(12) United States Patent
Sugimoto

(10) Patent No.: US 12,220,679 B2
(45) Date of Patent: Feb. 11, 2025

(54) DEOXIDANT COMPOSITION

(71) Applicant: Mitsubishi Gas Chemical Company, Inc., Tokyo (JP)

(72) Inventor: Ken Sugimoto, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 528 days.

(21) Appl. No.: 17/414,276

(22) PCT Filed: Nov. 26, 2019

(86) PCT No.: PCT/JP2019/046126
§ 371 (c)(1),
(2) Date: Jun. 15, 2021

(87) PCT Pub. No.: WO2020/129547
PCT Pub. Date: Jun. 25, 2020

(65) Prior Publication Data
US 2022/0072503 A1    Mar. 10, 2022

(30) Foreign Application Priority Data

Dec. 18, 2018   (JP) ................................ 2018-236497

(51) Int. Cl.
| | | |
|---|---|---|
| *B01J 20/02* | (2006.01) | |
| *A61K 47/02* | (2006.01) | |
| *B01D 53/14* | (2006.01) | |
| *B01J 20/14* | (2006.01) | |
| *B01J 20/16* | (2006.01) | |
| *B01J 20/20* | (2006.01) | |
| *B01J 20/28* | (2006.01) | |
| *B65D 81/26* | (2006.01) | |
| *G01B 7/02* | (2006.01) | |
| *G01B 7/06* | (2006.01) | |
| *G01N 27/02* | (2006.01) | |
| *G01N 27/72* | (2006.01) | |
| *G01N 27/90* | (2021.01) | |
| *G01V 3/10* | (2006.01) | |

(52) U.S. Cl.
CPC ...... *B01J 20/0229* (2013.01); *B01D 53/1493* (2013.01); *B01J 20/14* (2013.01); *B01J 20/165* (2013.01); *B01J 20/20* (2013.01); *B01J 20/28016* (2013.01); *B65D 81/266* (2013.01); *G01N 27/023* (2013.01); *G01N 27/72* (2013.01); *G01N 27/9046* (2013.01); *G01V 3/10* (2013.01); *A61K 47/02* (2013.01); *B01D 2252/10* (2013.01); *G01B 7/023* (2013.01); *G01B 7/10* (2013.01); *G01B 7/105* (2013.01)

(58) Field of Classification Search
CPC ...... B01J 20/0229; B01J 20/14; B01J 20/165; B01J 20/20; B01J 20/28016; B01J 20/12; B01J 20/28011; B01J 20/28035; B01J 20/103; B01J 20/02; B01J 20/24; B01D 53/1493; B01D 2252/10; B01D 2253/11; B01D 2257/104; B01D 53/02; B01D 53/14; B65D 81/266; B65D 81/26; G01V 3/10; A61K 47/02; G01N 27/9046; G01N 27/72; G01N 27/023; G01B 7/023; G01B 7/10; G01B 7/105
USPC ............................ 324/51, 55, 200, 228, 234
See application file for complete search history.

(56) References Cited

U.S. PATENT DOCUMENTS

| | | | |
|---|---|---|---|
| 7,432,715 B2 | 10/2008 | Stamatescu | |
| 2009/0095941 A1 | 4/2009 | Nakata et al. | |
| 2009/0159846 A1* | 6/2009 | Sugimoto | ................ B01J 20/12 252/188.28 |
| 2011/0172091 A1* | 7/2011 | Sugimoto | .......... B01J 20/28042 502/404 |
| 2015/0276964 A1 | 10/2015 | McAdam | |
| 2019/0083955 A1* | 3/2019 | Sugimoto | ................ B01J 20/28 |
| 2022/0226799 A1* | 7/2022 | Sato | ...................... A23L 3/3436 |
| 2023/0173453 A1* | 6/2023 | Sato | ................... B01J 20/28004 502/412 |

FOREIGN PATENT DOCUMENTS

| | | | | |
|---|---|---|---|---|
| CN | 1961222 A | 5/2007 | | |
| CN | 101304806 A | 11/2008 | | |
| CN | 102342564 A | 2/2012 | | |
| CN | 202213755 U | 5/2012 | | |
| CN | 103478247 A | 1/2014 | | |
| CN | 204124439 U | 1/2015 | | |
| CN | 104950336 A | 9/2015 | | |
| CN | 205982669 U | 2/2017 | | |
| CN | 108472577 A | 8/2018 | | |
| EP | 1974808 A1 | 10/2008 | | |
| JP | H08-38883 A | 2/1996 | | |
| JP | H0838883 | * | 2/1996 | .............. C23F 15/00 |
| JP | H11-226388 A | 8/1999 | | |
| JP | H11226388 | * | 8/1999 | .......... A23L 3/3436 |
| JP | 2005-345382 A | 12/2005 | | |
| JP | 2017-030813 A | 2/2017 | | |

(Continued)

OTHER PUBLICATIONS

JP WO2017/169015 Machine Translation, Apr. 5, 2018 (Year: 2018).*
Gaikwad et al., "Oxygen scavenging films in food packaging," Environmental Chemistry Letters, 2018, vol. 16, pp. 523-538.
Food Packaging Technology, edited by Coles et al., Blackwell Publishing Ltd., translated into Chinese by China Light Industry Press, 2012 (3 pages).

(Continued)

*Primary Examiner* — Raul J Rios Russo
(74) *Attorney, Agent, or Firm* — Fitch, Even, Tabin & Flannery LLP

(57) ABSTRACT

An oxygen scavenger composition comprising iron having a metallic iron content of 94% by mass or more.

20 Claims, No Drawings

(56) References Cited

FOREIGN PATENT DOCUMENTS

WO 2017/169015 A1 10/2017

OTHER PUBLICATIONS

Food Packaging Technology, edited by Coles et al., Blackwell Publishing Ltd., 2003, pp. 284-285.
International Search Report for PCT/JP2019/046126, mailed Mar. 3, 2020, and English Translation submitted herewith (5 pages).
Biji, K.B. et al., "Smart packaging systems for food applications: a review," Journal of Food Science and Technology, 2015, vol. 52, No. 10, pp. 6125-6135.
Cruz, R.S. et al., "Oxygen Scavengers: An Approach on Food Preservation," Structure and Function of Food Engineering, 2012, pp. 21-42.
Gaikwad, K.K. et al., "Oxygen scavenging films in food packaging," Environmental Chemistry Letters, 2018, vol. 16, pp. 523-538.
Kuswandi, B. et al., "Smart packaging: sensors for monitoring of food quality and safety," Sensing and Instrumentation for Food Quality and Safety, 2011, vol. 5, pp. 137-146.
Ries, B., "Overcoming Noise in Food Metal Detectors," 2018, available at https://www.thermofisher.com/blog/food/overcoming-noise-to-detect-small-metal-pieces-in-packaged-foods/ (1 page).
Shao, Zhong et al., "Electrical Materials," China Coal Industry Publishing House (1994), p. 135.
Zeng, Qingzhu et al., "Food Safety Technology," China Commercial Publishing House, (2008), pp. 39-40.

\* cited by examiner

DEOXIDANT COMPOSITION

CROSS-REFERENCE TO RELATED APPLICATIONS

This application is a U.S. national phase application filed under 35 U.S.C. § 371 of International Application Number PCT/JP2019/046126, filed Nov. 26, 2019, designating the United States, which claims priority from Japanese Application Number 2018-236497, filed Dec. 18, 2018.

FIELD OF THE INVENTION

The present invention relates to an oxygen scavenger composition, particularly relates to an iron-based oxygen scavenger composition.

BACKGROUND OF THE INVENTION

A method of using an oxygen scavenger is known as a technique for storage of a food, a pharmaceutical product, or the like. In this method, an article to be stored and the oxygen scavenger can be enclosed and sealed in a sealed container having gas barrier properties, thereby allowing oxygen in the sealed container to be absorbed by the oxygen scavenger and thus allowing the atmosphere in the sealed container to be retained in a substantially oxygen-free state. Representative examples of the oxygen scavenger include an iron-based oxygen scavenger containing iron as a main agent, and a non-iron-based oxygen scavenger containing ascorbic acid, glycerin, or the like as a main agent. The type of the oxygen scavenger is appropriately selected depending on the intended use, and such an iron-based oxygen scavenger is widely used from the viewpoint of oxygen absorption performance.

It is importantly confirmed from the viewpoint of quality retention of a food, a pharmaceutical product, or the like that the oxygen scavenger is properly enclosed in a product such as a food or a pharmaceutical product.

An iron-based oxygen scavenger can be detected by a metal detecting machine, and thus the presence of such an oxygen scavenger in a product can be relatively easily confirmed.

A non-iron-based oxygen scavenger is not generally detected by a metal detecting machine, and thus no metal detecting machine can be used and an expensive X-ray foreign material detector is required to be used as a unit for confirming the presence of such an oxygen scavenger in a product. In this regard, for example, Patent Literature 1 discloses an oxygen scavenger package comprising a non-iron-based oxygen absorbing substance and iron oxide, for the purpose of providing an oxygen scavenger package and a method of confirming the presence of thereof, which not only can allow the presence of the oxygen scavenger package in a tightly sealed container to be detected by a metal detecting machine, but also can allow incorporation of stainless steel widely used in a production process of a food, a pharmaceutical product, or the like to be detected, even in a case where such stainless steel is incorporated as a foreign material.

Meanwhile, in order to prevent a metallic foreign material such as metal debris from being incorporated into a product such as a food or a pharmaceutical product in a production process of the product and to prevent the product from being shipped as it is, the presence of the metallic foreign material in the product is inspected by a metal detecting machine. In particular, in recent years, there has been increased in awareness of consumers about safety of foods, pharmaceutical products, and the like, and there has been focused on troubles of incorporation of foreign materials. Thus, producers are demanded to further pay attention to incorporation of metallic foreign materials.

It is necessary for detection of a metallic foreign material in a product enclosing an iron-based oxygen scavenger by use of a metal detecting machine to distinguish and detect iron comprised in the metallic foreign material and iron comprised in the oxygen scavenger. In general, in a case where a plurality of detection targets are present, a detection signal derived from each of the detection targets is specified and any uninvolved detection signal is canceled as a noise, resulting in an enhancement in sensitivity of any involved detection signal. However, even if any detection signal derived from an iron-based oxygen scavenger is tried to be canceled as a noise, such any detection signal is large in variation and thus the iron-based oxygen scavenger cannot be sufficiently specified. Thus, there is currently performed generally a method involving detecting a metallic foreign material in a product by a metal detecting machine, thereafter enclosing an iron-based oxygen scavenger in the product, and thereafter further confirming the presence of the iron-based oxygen scavenger by the metal detecting machine.

CITATION LIST

Patent Literature

Patent Literature 1: JP 2017-030813 A

SUMMARY OF INVENTION

Technical Problem

It is demanded to efficiently detect a metallic foreign material in a product enclosing an iron-based oxygen scavenger, by use of a metal detecting machine. In particular, it is highly demanded, in view of an increase in awareness of consumers about safety of foods, pharmaceutical products, and the like, to detect a metallic foreign material even after enclosure of an oxygen scavenger.

Accordingly, an object of the present invention is to provide an iron-based oxygen scavenger that does not inhibit any detection of a metallic foreign material by a metal detecting machine.

Solution to Problem

The present inventor has made studies about the reason for a large variation in detection signal derived from a conventional iron-based oxygen scavenger. The surface of iron comprised in a conventional iron-based oxygen scavenger has been slightly oxidized in order to enhance oxygen absorption performance, and such iron has been changed into a mixture of a plurality of iron oxides due to such oxidation. Such iron oxides are different in magnetic properties depending on the respective oxidation numbers thereof, and thus the present inventor has focused on an increase in variation in detection signal in a metal detecting machine whose detection principle is according to the change in magnetic force. The present inventor has further made intensive studies, and as a result, has found that an increase in purity of iron in an oxygen scavenger suppresses oxidation of iron and stabilizes magnetic properties, thereby enabling a detection signal derived from iron to be specified. The present invention has been completed based on such a finding.

That is, the present invention relates to the following.

<1> An oxygen scavenger composition comprising iron having a metallic iron content of 94% by mass or more.
<2> The oxygen scavenger composition according to <1>, comprising a powdery/granular material having an α layer comprising a water retention agent, a swelling agent, a metal salt and water, a β layer comprising iron having a metallic iron content of 94% by mass or more, and a γ layer comprising a porous carrier,
wherein, in the powdery/granular material, a layered structure is formed including the α layer, the β layer and the γ layer in the listed order from an inside to an outside of the powdery/granular material.
<3> The oxygen scavenger composition according to <2>, wherein the water retention agent comprises at least one selected from the group consisting of diatomaceous earth, silica and activated carbon.
<4> The oxygen scavenger composition according to <2> or <3>, wherein the swelling agent comprises at least one selected from the group consisting of calcium carboxymethyl cellulose, sodium carboxymethyl cellulose, calcium bentonite and sodium bentonite.
<5> The oxygen scavenger composition according to any one of <2> to <4>, wherein the powdery/granular material comprises 30% by mass or more and 50% by mass or less of the α layer, 49% by mass or more and 69% by mass or less of the β layer, and 0.1% by mass or more and 5.0% by mass or less of the γ layer, based on a total amount of the powdery/granular material.
<6> The oxygen scavenger composition according to any one of <2> to <5>, wherein the α layer comprises 1.0% by mass or more and 10% by mass or less of the swelling agent based on a total amount of the α layer.
<7> A method of inspecting a foreign material in a product enclosing the oxygen scavenger composition according to any one of <1> to <6> by a metal detecting machine, the method comprising
a step of canceling a detection signal derived from the iron comprised in the oxygen scavenger composition as a noise.
<8> A method of inspecting a product which is a product enclosing the oxygen scavenger composition according to any one of <1> to <6> by a metal detecting machine, the method comprising
performing detection by simultaneously using two or more frequency detectors, to simultaneously confirm the presence of the oxygen scavenger composition and inspect a foreign material.

Advantageous Effects of Invention

The oxygen scavenger composition of the present invention is stable in magnetic properties of iron comprised therein, thus can allow a detection signal of iron, derived from the oxygen scavenger composition, to be canceled as a noise at a high accuracy, and does not inhibit detection of a metallic foreign material by a metal detecting machine. Thus, a metallic foreign material can be detected at a high sensitivity, even after an iron-based oxygen scavenger composition is enclosed in a product such as a food or a pharmaceutical product. Furthermore, a metal detecting machine provided with two or more frequency detectors can be used to perform detection, thereby simultaneously confirm the presence of the oxygen scavenger composition and detect a metallic foreign material.

DESCRIPTION OF EMBODIMENTS

Hereinafter, one embodiment of the present invention will be described. The content of the present invention is not limited to any embodiment described below.

The term "A to B" with respect to the designation of numerical values herein means "A or more and B or less" (A<B) or "A or less and B or more" (A>B). A combination of preferable aspects of the present invention corresponds to a more preferable aspect.

[Oxygen Scavenger Composition]

The oxygen scavenger composition of the present invention comprises iron having a metallic iron content of 94% by mass or more. The metallic iron content of iron comprised in the oxygen scavenger composition is preferably 95% by mass or more, more preferably 96% by mass or more, further preferably 96.5% by mass or more, more further preferably 97% by mass or more, more further preferably 98% by mass or more, more further preferably 99% by mass or more. The upper limit of the metallic iron content is not particularly limited, and may be 100% by mass or less, may be 99.9% by mass or less, or may be 99.5% by mass or less. The metallic iron content of iron comprised in the oxygen scavenger composition is 94% by mass or more, and thus magnetic properties of iron are stabilized and a detection signal derived from iron can be specified by a metal detecting machine whose detection principle is according to the change in magnetic force.

The metallic iron content of iron comprised in the oxygen scavenger composition herein is measured according to the Bromine-Methanol dissolution EDTA titration method described in Commentary 5 of JIS M8213-1995 "Iron ores-Method for determination of acid soluble iron (II) content". Specifically, a sample (iron) is dissolved in bromine-methanol, and the residue is filtered. A certain amount of the filtrate is fractionated, iron is oxidized by ammonium persulfate, and thereafter an ammonium acetate solution is added to adjust the pH to 2.0±0.2. Finally, titration is made by an EDTA 2Na standard solution with sulfosalicylic acid as an indicator.

In a case where each production step is made under an atmosphere of an inert gas such as nitrogen as in one embodiment of the method of producing the oxygen scavenger composition of the present invention, described below, metallic iron as a starting material is not oxidized in such each production step and thus the metallic iron content comprised in an oxygen scavenger obtained can be quantitatively determined as the same content as that of such metallic iron as a starting material.

In a case where the oxygen scavenger composition comprises any component other than iron, an iron component can be separated by a magnet in advance and the amount of metallic iron can be quantitatively determined by the above analysis method.

In the case of an oxygen scavenger composition having a multilayered structure including the α layer, the β layer and the γ layer, according to one embodiment of the present invention, the purity of metallic iron can be measured by pulverizing the oxygen scavenger composition by a mortar or the like in advance and thereafter subjecting the pulverized product to the above analysis method.

In order that the metallic iron content of iron comprised in the oxygen scavenger composition of the present invention is 94% by mass or more, the oxygen scavenger composition is preferably produced by using iron (so-called pure iron) having a metallic iron content of 99.0% by mass or more or a secondary reduced iron powder enhanced in purity by performing a reduction step twice, as a starting material. The oxygen scavenger composition is also preferably produced under a nitrogen atmosphere, from the viewpoint of suppression of oxidization of iron in production of the oxygen scavenger composition.

Iron is known to be more difficult to oxidize as it has a higher purity. Thus, a conventional iron-based oxygen scavenger has been produced with the surface of iron being intendedly slightly oxidized from the viewpoint of search of oxygen absorption performance, and the metallic iron content has been at most about 93% by mass.

As described above, iron in a conventional iron-based oxygen scavenger has been changed into a mixture of a plurality of iron oxides due to oxidization, and a ferromagnetic substance, a non-magnetic substance and a soft magnetic material has been mixed and present. Such iron oxides are different in magnetic properties depending on the respective oxidation numbers, and thus the variation in detection signal is larger in a metal detecting machine whose detection principle is according to the change in magnetic force. On the contrary, the oxygen scavenger composition of the present invention, which comprises iron at a high purity, thus allows oxidation of iron in the oxygen scavenger to be suppressed, from the viewpoint that magnetic properties of iron are stabilized to suppress the variation in detection signal in a metal detecting machine.

The shape of iron comprised in the oxygen scavenger composition is not particularly limited, and is preferably an iron powder from the viewpoints of oxygen absorption performance, availability and ease of handling. The iron powder is not particularly limited as long as the surface of iron is exposed, and, for example, a reduced iron powder, an electrolytic iron powder or an atomized iron powder can be suitably used. Alternatively, a pulverized product or a cutting chip of cast iron or the like can also be used.

Such iron powders can be used singly or, if necessary, in combinations of two or more kinds thereof. Such iron powders can be each easily obtained in the form of a commercially available product. In a case where a combination of two or more kinds is used as iron, the metallic iron content of iron as a whole is required to be 94% by mass or more.

An iron powder whose surface is covered with a metal halide can also be used. Such an iron powder covered with a metal halide can be prepared by mixing such an iron powder with an aqueous solution of a metal halide, and then drying a mixture to remove moisture.

The average particle size of the iron powder is preferably 1 mm or less, more preferably 500 μm or less, further preferably 100 μm or less from the viewpoint of an improvement in contact with oxygen, and is preferably 1 μm or more, more preferably 10 μm or more, further preferably 20 μm or more, more further preferably 40 μm or more, particularly preferably 53 μm or more from the viewpoint of suppression of the occurrence of dust. The particle size here mentioned represents a particle size determined from a weight fraction with respect to the size of a standard sieve according to ISO 3310-1:2000 (corresponding to JIS Z8801-1:2006) after vibration for 5 minutes.

The oxygen scavenger composition of the present invention comprises iron as a main agent. The content ratio of iron in the oxygen scavenger composition relative to the oxygen scavenger composition is preferably 40 to 90% by mass, more preferably 45 to 80% by mass, further preferably 50 to 70% by mass, more further preferably 50 to 65% by mass, particularly preferably 52 to 60% by mass.

Two kinds of oxygen scavengers, moisture-dependent type and self-reactive type oxygen scavengers, are known. The moisture-dependent type oxygen scavenger is contacted with moisture evaporated from a product such as a food or a pharmaceutical product to thereby perform oxygen absorption, and the self-reactive type oxygen scavenger has moisture necessary for a reaction in the oxygen scavenger, and is contacted with air to thereby perform oxygen absorption. The oxygen scavenger composition of the present invention may be any of the moisture-dependent type and the self-reactive type oxygen scavengers, and is preferably the self-reactive type oxygen scavenger.

The oxygen scavenger composition of the present invention preferably comprises water, a water retention agent, a swelling agent and a metal salt as components other than iron.

(Water)

The oxygen scavenger composition of the present invention preferably comprises water from the viewpoint that the iron-based oxygen scavenger exhibits oxygen absorption performance. The content of in water in the oxygen scavenger composition is preferably 20 to 60 parts by mass, more preferably 25 to 55 parts by mass, further preferably 40 to 50 parts by mass, more further preferably 44 to 48 parts by mass based on 100 parts by mass of iron from the viewpoint of oxygen absorption performance.

(Water Retention Agent)

In a case where the oxygen scavenger composition of the present invention comprises water, the oxygen scavenger composition of the present invention preferably comprises a water retention agent from the viewpoint of an improvement in handleability of the oxygen scavenger composition. The water retention agent is a substance which can allow water to be not leaked out but retained by impregnating water therewith.

The water retention agent is not particularly limited as long as it can retain water, and a generally available porous substance or a high water-absorbing resin can be used. The porous substance is not particularly limited, and examples thereof include diatomaceous earth, zeolite, sepiolite, cristobalite, porous glass, silica, activated earth, acid earth, activated carbon, vermiculite and a wood powder. The high water-absorbing resin is not particularly limited, and examples thereof include a polyacrylate-based resin, a polysulfonate-based resin, a polyacrylamide-based resin, a polyvinyl alcohol-based resin, a starch-based resin, a cellulose-based resin and a polyalginic acid-based resin. The water retention agent preferably comprises at least one selected from the group consisting of diatomaceous earth, silica and activated carbon, more preferably comprises activated carbon, further preferably a combination of activated carbon with a porous substance other than activated carbon, or a high water-absorbing resin, more further preferably a combination of activated carbon with a porous substance other than activated carbon, more further preferably a combination of activated carbon with diatomaceous earth or silica. Such water retention agents can be used singly or, if necessary, in combinations of two or more kinds thereof. Such water retention agents can be each easily obtained in the form of a commercially available product.

Activated carbon among such water retention agents is particularly preferable because of having not only a water retention function, but also a function of promoting an oxidation reaction of iron. The type of activated carbon is not particularly limited, and may be any of, for example, a wood material, a palm shell and coal.

Activated carbon, which contains moisture, can be used as it is, and the water content ratio of activated carbon is preferably 30% by mass or more, more preferably 40% by mass or more.

Water in the oxygen scavenger composition also encompasses water contained in activated carbon.

The water retention agent is not particularly limited in terms of characteristics thereof, one in the form of a powder high in fluidity is suitably used from the viewpoint of handleability in production of the oxygen scavenger, and one having a shape close to a spherical shape is more preferable. The average particle size of the water retention agent is preferably 10 μm or more and 1000 μm or less, more preferably 100 μm or more and 500 μm or less from the viewpoint of handleability in production of the oxygen scavenger. The average particle size of the water retention agent is in the range, resulting in tendencies to easily maintain the shape of an α layer described below and to enable a more stabilized powdery/granular material to be formed. The particle of the water retention agent here used can be any of a primary particle, an aggregated particle and an agglomerated material regardless of the form, as long as the particle has a size in the range. The water retention agent having a particle size in the range can also be used singly, or can also be used as a mixture of a plurality of such agents different in particle size, at any ratio.

The content of the water retention agent in the oxygen scavenger composition is not particularly limited, and is preferably 20 to 500 parts by mass, more preferably 30 to 300 parts by mass, further preferably 40 to 200 parts by mass based on 100 parts by mass of water. In a case where activated carbon is comprised, the content of activated carbon in the oxygen scavenger composition is not particularly limited, and is preferably 20% by mass or less, more preferably 15% by mass or less, further preferably 10% by mass or less, more further preferably 6% by mass or less, more further preferably 5% by mass or less, based on the total amount of the oxygen scavenger composition. Activated carbon is preferably comprised because the oxygen scavenger composition can be more enhanced in oxygen absorption performance under a low-humidity atmosphere at 50% RH or less.

(Swelling Agent)

In a case where the oxygen scavenger composition of the present invention comprises water, the oxygen scavenger composition of the present invention preferably comprises a swelling agent from the viewpoint of moldability in production of the oxygen scavenger composition. The swelling agent is a component that is swollen by moisture to thereby inhibit no deoxygenation reaction by pressure molding, and is preferably used in the state of being substantially dried or in the state of being semi-swollen or swollen with absorption of a small amount or required amount of water. The swelling agent preferably has, in addition to the above function, any one of a function as a lubricant that facilitates extrusion of a mixture in production, in particular, production according to a continuous pressure molding method, and a function as a binding agent that allows the shape of a pressure molded article to be retained, and particularly preferably has both the functions. The swelling agent can have a binding function that allows the shape of an α layer described below to be retained.

The swelling agent is not particularly limited as long as it is a commonly known swelling agent, and a known swelling agent for use in foods or the like, for example, an inorganic swelling agent, an organic swelling agent, an adhesive agent, a pressure-sensitive adhesive and a binder can be each used.

Examples of the inorganic swelling agent include clay minerals such as sodium bentonite, calcium bentonite and sodium montmorillonite. Examples of the organic swelling agent include organic bentonite; natural substances such as defatted frozen bean curd, agar, starch, dextrin, gum arabic, gelatin and casein; semisynthetic articles such as crystalline cellulose, carboxymethyl cellulose, sodium carboxymethyl cellulose, calcium carboxymethyl cellulose, hydroxyethyl cellulose, ligninsulfonic acid and hydroxyethylated starch; and synthetic articles such as water-insolubilized polyvinyl alcohol and polyvinyl methyl ether. Such swelling agents can be used singly or, if necessary, in combinations of two or more kinds thereof, are preferably the inorganic swelling agent and the organic swelling agent, and more preferably correspond to a combination of the inorganic swelling agent with the organic swelling agent. Such swelling agents can be each easily obtained in the form of a commercially available product.

A clay mineral is preferable because of being inexpensive and excellent in performance. A clay mineral is known as inorganic soap, and has a function as a lubricant. A clay mineral swollen by water is known to exhibit high thixotropic properties, and is preferable because of also exhibiting binding properties. A cellulose-based semisynthetic article is preferable because of exhibiting excellent swelling properties. In particular, for example, bentonites such as calcium bentonite and sodium bentonite, and carboxymethyl cellulose, sodium carboxymethyl cellulose, calcium carboxymethyl cellulose and the like are preferable because of being inexpensive and strong in binding force. The swelling agent preferably contains at least one selected from the group consisting of calcium carboxymethyl cellulose, sodium carboxymethyl cellulose, calcium bentonite and sodium bentonite.

In particular, a clay mineral and a cellulose-based semisynthetic article is more preferably used in combination, and any bentonite and a cellulose-based semisynthetic article is further preferably used in combination.

The average particle size of the swelling agent is preferably 0.001 μm or more and 10 μm or less, more preferably 0.01 μm or more and 1.0 μm or less from the viewpoint of suppression of the occurrence of dust and from the viewpoint of a binding function.

The content of the swelling agent in the oxygen scavenger composition is preferably about 1 to 20% by mass, more preferably about 1 to 15% by mass, further preferably about 1.5 to 12% by mass relative to the oxygen scavenger composition. The content based on 100 parts by mass of iron is preferably 2 to 15 parts by mass, more preferably about 2 to 10 parts by mass, further preferably about 3 to 10 parts by mass, more further preferably about 4 to 10 parts by mass. The content based on 100 parts by mass of water is preferably 3 to 30 parts by mass, more preferably 5 to 20 parts by mass, more preferably 7 to 15 parts by mass.

(Metal Salt)

The oxygen scavenger composition of the present invention preferably comprises a metal salt from the viewpoint that a higher oxygen absorption ability is exhibited. The metal salt catalytically acts on an oxidation reaction of iron, resulting in an enhancement in activity of iron. The metal salt serves to attract moisture in an atmosphere in the case of the moisture-dependent type oxygen scavenger, and serves to prevent moisture from being evaporated in a low-humidity atmosphere and lost from the oxygen scavenger in the case of the self-reactive type oxygen scavenger.

The metal salt is not particularly limited, and a metal halide is preferable. The metal halide here used can be any commonly known one without particular limitation.

The metal in the metal halide is not particularly limited, and examples thereof include at least one selected from the group consisting of an alkali metal, an alkali earth metal, copper, zinc, aluminum, tin, iron, cobalt and nickel. In particular, at least one selected from the group consisting of lithium, potassium, sodium, magnesium, calcium, barium and iron is more preferable, and at least one selected from the group consisting of potassium, sodium and calcium is more preferable. The halide in the metal halide is not particularly limited, and examples thereof include chloride, bromide and iodide.

The metal halide is preferably calcium chloride, sodium chloride, calcium bromide, sodium bromide, calcium iodide or sodium iodide, more preferably calcium chloride or sodium chloride, from the viewpoints of handleability, safety and the like.

Such metal salts can be used singly or, if necessary, in combinations of two or more kinds thereof. Such metal salts can be each easily obtained in the form of a commercially available product.

The content of the metal salt in the oxygen scavenger composition is preferably 0.5 to 15% by mass, more preferably 1 to 10% by mass on a weight basis in the composition. The content of the metal salt based on 100 parts by mass of iron is preferably 0.5 to 20 parts by mass, more preferably 2 to 10 parts by mass.

In preferable one embodiment, the oxygen scavenger composition of the present invention preferably comprises a powdery/granular material having an α layer comprising a water retention agent, a swelling agent, a metal salt and water, a β layer comprising iron having a metallic iron content of 94% by mass or more, and a γ layer comprising a porous carrier, and in the powdery/granular material, a layered structure is preferably formed including the α layer, the β layer and the γ layer in the listed order from the inside to the outside of the powdery/granular material.

The oxygen scavenger composition of the present invention having the above layered structure (core-shell structure) not only is excellent in amount of absorption of oxygen per unit volume even in the form of the oxygen scavenger composition of the present invention, comprising iron which is high in purity and difficult to oxidize, and has the effect of not inhibiting detection of a metallic foreign material by a metal detecting machine, but also can exhibit high oxygen absorption performance. The configuration according to the embodiment can also allow the amount of iron used to be reduced due to a high oxidation reaction efficiency. While the reason why such high oxygen absorption performance is exhibited is not clear, it is considered as follows. It is considered that a layer comprising iron is adjacent outside a layer comprising water to thereby easily bring iron into contact with water and oxygen, promoting an oxidation reaction, and a layer of a porous carrier, located further outward, has an improved fluidity and thus is enhanced in packing properties to thereby increase the amount of absorption of oxygen per unit volume.

The oxygen scavenger composition of the present embodiment, which has the core-shell structure, preferably comprises a powdery/granular material having an α layer (hereinafter, also simply referred to as "α layer") comprising a water retention agent, a swelling agent, a metal salt and water, a β layer (hereinafter, also simply referred to as "β layer") comprising iron and a γ layer (hereinafter, also simply referred to as "γ layer") comprising a porous carrier.

Herein, iron and the water retention agent in the oxygen scavenger composition of the present embodiment are not separated in discrete powdery/granular materials unlike a conventional oxygen scavenger composition, and are preferably integrated as a layered structure including the α layer comprising the water retention agent and the β layer comprising iron. In the powdery/granular material, a layered structure is preferably formed including the α layer, the β layer and the γ layer in the listed order from the inside to the outside of the powdery/granular material.

The powdery/granular material comprised in the oxygen scavenger composition of the present embodiment preferably has a layered structure including the α layer (inside), the β layer and the γ layer (outside) formed in the listed order from the inside to the outside of the powdery/granular material. The powdery/granular material in the oxygen scavenger composition of the present embodiment mainly has a layered structure including the α layer comprising the water retention agent and the β layer comprising iron formed in the listed order (hereinafter, also represented as "α layer/β layer/γ layer"), and thus the β layer comprising iron is adjacent outside the α layer comprising the water retention agent that supplies moisture, thereby not only allowing iron to be rapidly subjected to an oxidation reaction, but also allowing the oxidation reaction rate of iron and oxygen to be enhanced. Furthermore, such a layered structure can enhance the oxidation reaction rate of iron and oxygen without, for example, any design for secondary processing of iron into a flattened shape or the like and expanding the field of the oxidation reaction of iron and oxygen.

The γ layer comprising a silica compound or the like is adjacent outside the β layer, thereby improving slipping properties of the powdery/granular material to allow the powdery/granular material to be closely packed, resulting in an increase in amount of absorption of oxygen per unit volume, of the oxygen scavenger composition.

Herein, "the layered structure including the α layer, the β layer and the γ layer in the listed order" refers to a structure in which the β layer and the α layer are formed in the air space of the γ layer, and the α layer is formed in the air space of the β layer. Accordingly, the layered structure encompasses not only a structure in which the surfaces of the β layer and the α layer are covered with the γ layer, but also a structure in which the β layer and the α layer are packed in one portion of the air space of a three dimensional network structure with the γ layer, and similarly encompasses not only a structure in which the surface of the α layer is covered with the β layer, but also a structure in which the α layer is packed in one portion of the air space of a three dimensional network structure with the β layer. Accordingly, "the layered structure including the α layer, the β layer and the γ layer in the listed order" herein also encompasses a structure of a powdery/granular material in which the boundary among the α layer, the β layer and the γ layer is not strictly clear. The powdery/granular material in the present embodiment may also be one further having a layer other than the α layer, the β layer and the γ layer. Furthermore, the oxygen scavenger composition of the present embodiment may comprise a powdery/granular material in which "the layered structure including the α layer, the β layer and the γ layer in the listed order" is formed, and may further comprise a powdery/granular material in which "the layered structure including the α layer, the β layer and the γ layer in the listed order" is not formed. The oxygen scavenger composition of the present embodiment may be, of course, an oxygen scavenger composition consisting of a powdery/granular material in which "the layered structure including the α layer, the β layer and the γ layer in the listed order" is formed.

The shape of the powdery/granular material in the present embodiment is not particularly limited, examples thereof include a spherical shape, an elliptical shape and a cylinder, and a spherical shape is preferable because packing properties tend to be more excellent.

The powdery/granular material in the present embodiment preferably comprises 30% by mass or more and 50% by mass or less of the α layer, 49% by mass or more and 69% by mass or less of the β layer, and 0.1% by mass or more and 5.0% by mass or less of the γ layer, based on the total amount (100% by mass) of the powdery/granular material. The contents of the α layer, the β layer and the γ layer in the powdery/granular material are in such respective ranges, resulting in tendencies to sufficiently supply moisture necessary for the oxidation reaction of iron, to provide a larger amount of absorption of oxygen, and to inhibit water in an amount unnecessary for the oxidation reaction of iron from being comprised.

The powdery/granular material more preferably comprises 35% by mass or more and 50% by mass or less, further preferably 40% by mass or more and 50% by mass or less of the α layer from the viewpoint of an enhancement in oxygen absorption properties. The powdery/granular material comprises 49% by mass or more and 69% by mass or less, more preferably 50% by mass or more and 65% by mass or less, further preferably 52% by mass or more and 60% by mass or less of the β layer. The powdery/granular material more preferably comprises 0.2% by mass or more and 3.0% by mass or less, further preferably 0.5% by mass or more and 2.0% by mass or less of the γ layer.

[α Layer]

The α layer in the present embodiment is a layer comprising a water retention agent, a swelling agent, a metal salt and water.

The α layer preferably comprises 10% by mass or more and 85% by mass or less, more preferably 30% by mass or more and 80% by mass or less of the water retention agent based on the total amount (100% by mass) of the α layer. The content of the water retention agent is 10% by mass or more, resulting in tendencies to enable the powdery/granular material to sufficiently retain water and to easily maintain the shape of the α layer, and the content of the water retention agent is 85% by mass or less, resulting in tendencies to allow the volume proportion of the α layer in the oxygen scavenger composition not to be too high and to more increase the amount of absorption of oxygen per unit volume of the oxygen scavenger composition.

The α layer preferably comprises 0.1% by mass or more and 20% by mass or less, more preferably 1.0% by mass or more and 10% by mass or less of the swelling agent based on the total amount (100% by mass) of the α layer. The content of the swelling agent is 0.1% by mass or more, resulting in a tendency to easily maintain the shape of the α layer, and the content of the swelling agent is 20% by mass or less, resulting in tendencies to allow the proportion of the water retention agent in the α layer not to be too low, not to reduce the amount of moisture supplied to iron of the β layer, and to more increase the amount of absorption of oxygen.

The α layer preferably comprises 30% by mass or more and 70% by mass or less, more preferably 40% by mass or more and 65% by mass or less of an aqueous metal salt solution based on the total amount (100% by mass) of the α layer. The content of the aqueous metal salt solution is 30% by mass or more, resulting in a tendency to supply moisture sufficient to iron of the β layer, and the content of the aqueous metal salt solution is 70% by mass or less, resulting in a tendency to allow the water retention agent to sufficiently retain water, transferring water to the β layer to wet the surface of iron and not to inhibit iron and oxygen from being contacted, and both the contents tend to allow the amount of absorption of oxygen to be more increased.

In a case where the metal salt is in the form of an aqueous solution and thus serves as a starting material, the concentration of the salt is preferably 5.0% by mass or more and 30% by mass or less, more preferably 10% by mass or more and 20% by mass or less. The concentration of the salt is 5.0% by mass or more, thereby inhibiting the action of catalyzing oxidization of iron from being decreased, and the concentration of the salt is 30% by mass or less, thereby enabling a reduction in vapor pressure of moisture to be suppressed. That is, the amount of evaporation of moisture is reduced and sufficient moisture is not supplied to an iron powder of the β layer, and both the concentrations can allow a decrease in amount of absorption of oxygen to be inhibited.

[β Layer]

The β layer in the present embodiment is a layer comprising iron. Iron may be comprised in the form of an iron powder, and is preferably in the form of an iron powder from the viewpoints of oxygen absorption performance, availability and ease of handling. The β layer may comprise only iron, or may further any aid other than iron.

The β layer preferably comprises 80% by mass or more and 100% by mass or less, more preferably 90% by mass or more and 100% by mass or less of iron based on the total amount (100% by mass) of the (3 layer. The β layer may be formed from only iron. The content of iron is 80% by mass or more, resulting in a tendency to provide an oxygen scavenger composition more excellent in amount of absorption of oxygen per unit volume.

(Aid)

The aid in the present embodiment has a function of preventing binding of the iron powder according to oxidization, and a function of increasing the fluidity of the oxygen scavenger composition to easily pack the oxygen scavenger composition in packaging of the oxygen scavenger composition in a packaging material by a packaging machine.

The aid is a powder of, for example, silica, hydrophobic silica, magnesium stearate, calcium stearate, activated carbon, zeolite, pearlite, diatomaceous earth, activated earth, kaolin, talc, bentonite, activated alumina, gypsum, silica alumina, calcium silicate, magnesium oxide, graphite, carbon black, aluminum hydroxide or iron oxide. Such aids can be each easily obtained in the form of a commercially available product.

The average particle size of the aid is preferably 0.001 μm or more and 10 μm or less, more preferably 0.01 μm or more and 1.0 μm. The average particle size is 0.001 μm or more, thereby inhibiting the aid from being flown in air, to enhance handleability, and the average particle size is 10 μm or less, resulting in a tendency to inhibit iron from being mutually bound.

[γ Layer]

The γ layer in the present embodiment is a layer comprising a porous carrier.

The porous carrier in the present embodiment is not particularly limited as long as it is a carrier having a form of a porous state. The porous state here refers to a state where many pores that can be confirmed by an electron microscope are present in the surface and the inside. The porous carrier here appropriately used can be any porous substance for use in the water retention agent described above, and is preferably a silica compound. The silica compound means one containing silicon dioxide ($SiO_2$) as a main component. The silica compound is used, resulting in an increase in amount of absorption of oxygen of a powdery/granular material obtained.

The silica compound for use in the present embodiment is not particularly limited, and examples thereof include hydrophobic silica, hydrophilic silica, wet silica, dry silica, silica gel, diatomaceous earth, acid earth, activated earth, pearlite, kaolin, talc and bentonite. Such porous carriers can be used singly or, if necessary, in combinations of two or more kinds thereof. Such porous carriers can be each easily obtained in the form of a commercially available product.

The γ layer preferably comprises 30% by mass or more, more preferably 50% by mass or more, further preferably 80% by mass or more, more further preferably 90% by mass or more, more further preferably 95% by mass or more of the porous carrier based on the total amount (100% by mass) of the γ layer. The upper limit is not limited and may be 100% by mass, the γ layer may be formed from only the porous carrier, and the γ layer is preferably formed from only the porous carrier from the viewpoint of an enhancement in amount of absorption of oxygen per unit volume of the oxygen scavenger composition. The content of the porous carrier is in the range, resulting in a tendency to more increase the amount of absorption of oxygen.

The average particle size of the oxygen scavenger composition of the present invention is preferably 0.3 mm or more and 5.0 mm or less, more preferably 0.5 mm or more and 2.0 mm or less. The average particle size is 0.3 mm or more, resulting in a tendency to suppress attachment to a portion of a packaging machine contacting with the powdery/granular material in packaging, due to static electricity or the like, and the average particle size is 5.0 mm or less, resulting in a tendency to suppress a reduction in amount of absorption of oxygen per unit volume due to an excessively increased air space of the powdery/granular material. For example, a sieve having an aperture of 0.3 mm and a sieve having an aperture of 2 mm may be used for sieving in order to obtain an oxygen scavenger composition having an average particle size in the range. The average particle size can be measured with, for example, a commercially available laser diffraction/scattering particle size distribution measurement apparatus ("LA-960" manufactured by Horiba Ltd.).

[Method of Producing Oxygen Scavenger Composition]

The method of producing the oxygen scavenger composition of the present invention is not particularly limited. The oxygen scavenger composition can be prepared by mixing iron and, if necessary, any component other than iron until uniform dispersion is obtained. A mixing apparatus is not particularly limited, and a Nauta mixer (manufactured by Hosokawa Micron Group) or a conical mixer (manufactured by Ohno Chemical Machinery Co., Ltd.) can be used as a specific example. A solid oxygen scavenger composition may also be obtained by pressure molding and, if necessary, granulating the oxygen scavenger composition.

One example of the method of producing the oxygen scavenger composition having the core-shell structure is represented below. The above water retention agent and swelling agent are loaded to a mixing apparatus, and an aqueous metal halide salt solution is loaded thereto preferably over several ten seconds with mixing the agents, thereby preparing a powdery/granular material forming the α layer. Examples of the mixing apparatus include Vertical Granulator (manufactured by Powrex Corporation), High Speed Mixer (manufactured by Earthtechnica Co., Ltd.) and a granulator (manufactured by Akirakiko Co., Ltd.). Next, an iron powder is loaded to the powdery/granular material (α layer) and mixed to allow the iron powder to be attached to the outside of the α layer, thereby preparing an (α layer/β layer) powdery/granular material having the α layer and the β layer outside thereof. Furthermore, a porous carrier, preferably hydrophobic silica is loaded to the (α layer/β layer) powdery/granular material and mixed to allow the porous carrier to be attached to the outside of the β layer, thereby preparing an (α layer/β layer/γ layer) powdery/granular material having the (α layer/β layer) and the γ layer outside thereof.

Since iron serving as a main agent of the oxygen scavenger reacts with oxygen, such a reaction with oxygen gradually progresses even in the case of the absence of water, the metal salt, and the like. A large amount of a mixture of such a main agent with a catalyst or the like is handled in a production process involving mixing, pressure molding, granulating, and the like. Accordingly, such each step of the production process is preferably performed in an inert atmosphere (in the case of a substantially sealed system, the system is usually in a reducing atmosphere containing no oxygen) and any heat removal procedure is preferably appropriately performed. The inert atmosphere is preferably a nitrogen atmosphere.

[Method of Inspecting Foreign Material]

The oxygen scavenger composition of the present invention comprises iron stable in magnetic properties, and thus a detection signal derived from the oxygen scavenger composition can be canceled as a noise at a high accuracy and detection of a metallic foreign material by a metal detecting machine is not inhibited. Therefore, detection of a metallic foreign material can be performed at a high sensitivity even after an iron-based oxygen scavenger composition is enclosed in a product such as a food or a pharmaceutical product.

That is, the method of inspecting a foreign material of the present invention is a method of inspecting a foreign material with respect to a product enclosing the oxygen scavenger composition of the present invention described above by a metal detecting machine, the method comprising a step of canceling a detection signal derived from the iron comprised in the oxygen scavenger composition as a noise. Specifically, the method of inspecting a foreign material of the present invention is a method of inspecting a foreign material with respect to a product enclosing a oxygen scavenger composition comprising iron having a metallic iron content of 94% by mass or more by a metal detecting machine, the method comprising a step of canceling a detection signal derived from the iron comprised in the oxygen scavenger composition as a noise.

The method of inspecting a foreign material of the present invention involves performing inspection by use of a metal detecting machine whose detection principle is according to the change in magnetic force. The metal detecting machine is not particularly limited, and a commercially available product can be used.

In general, a metal detecting machine detects the change in electromagnetic wave in passing of an inspection product through the metal detecting machine to thereby detect the presence of a metal (see, for example, JP 117-120435 A). In a case where the metal is a magnetic substance such as iron, nickel or cobalt, the metal is magnetized by the magnetic field generated from a transmission coil, and magnetic lines of force are drawn toward the metal. In a case where the metal is a non-magnetic substance such as stainless steel, aluminum or copper, an eddy current is generated in the metal due to the magnetic field generated from a transmission coil, and the magnetic field generated from a transmission coil is consumed as thermal energy, generating the magnetic field in the vicinity of the metal. Such magnetic fields are sensed by a receiver coil, and thus the presence of the metal is detected.

It is necessary for detection of a metallic foreign material with respect to a product enclosing an iron-based oxygen scavenger, by use of a metal detecting machine, to distinguish and detect iron comprised in the metallic foreign material and iron comprised in the oxygen scavenger. In a case where the metallic foreign material is a magnetic substance, iron comprised in the oxygen scavenger is also a magnetic substance, and thus the metallic foreign material and the oxygen scavenger cannot be distinguished simply by only detection of the presence of the magnetic substance. It is necessary to cancel a detection signal derived from the iron-based oxygen scavenger, as a noise, thereby detecting only the metallic foreign material.

Iron comprised in a conventional iron-based oxygen scavenger, where the surface thereof has been intendedly slightly oxidized from the viewpoint of search of oxygen absorption performance, has been present indeterminately as a mixture of a plurality of iron oxides. Such iron oxides are different in magnetic properties depending on the respective oxidation numbers, and thus, even if any detection signal derived from the iron-based oxygen scavenger is tried to be canceled as a noise, the variation in detection signal is large and the iron-based oxygen scavenger cannot be sufficiently specified.

On the contrary, iron comprised in the oxygen scavenger composition of the present invention has a metallic iron content of 94% by mass or more and thus has a high purity and is stable in magnetic properties, and a detection signal derived from the oxygen scavenger composition can be specified. Thus, the method of inspecting a foreign material of the present invention can allow a detection signal derived from iron comprised in the oxygen scavenger composition to be canceled as a noise, thereby detecting a metallic foreign material at a high sensitivity.

In general, in a case where a plurality of detection targets are present, a detection signal derived from each of the detection targets is specified and any uninvolved detection signal is canceled as a noise, resulting in an enhancement in sensitivity of any involved detection signal (see, for example, JP 117-120435 A). A known means can also be applied as a means for canceling a detection signal as a noise, in the method of inspecting a foreign material of the present invention.

[Method of Inspecting Product (Method of Inspecting Product, Involving Simultaneously Confirming Presence of Oxygen Scavenger Composition and Inspecting Foreign Material)]

The method of inspecting a product of the present invention is a method of inspecting a product which is a product enclosing the oxygen scavenger composition of the present invention described above by a metal detecting machine, the method comprising performing detection by simultaneously using two or more frequency detectors, to simultaneously confirm the presence of the oxygen scavenger composition and inspect a foreign material. That is, the method of inspecting a product of the present invention is a method of inspecting a product which is a product enclosing the oxygen scavenger composition comprising iron having a metallic iron content of 94% by mass or more by a metal detecting machine, the method comprising performing detection by simultaneously using two or more frequency detectors, to simultaneously confirm the presence of the oxygen scavenger composition and inspect a foreign material.

A non-magnetic substance is high in detection sensitivity at a high frequency, as compared with a magnetic substance. Thus, a magnetic substance and a non-magnetic substance can be simultaneously detected by simultaneously using two or more frequency detectors to perform detection at a low frequency by one detector and perform detection at a high frequency by other detector (see, for example, JP 2005-345382 A).

As described above, iron comprised in the oxygen scavenger composition of the present invention has a metallic iron content of 94% by mass or more and has a high purity, and is stable in magnetic properties, and thus a detection signal derived from the oxygen scavenger composition can be specified. Therefore, the method of inspecting a product of the present invention can simultaneously use two or more frequency detectors to thereby not only simultaneously detect a magnetic substance and a non-magnetic substance, but also specify a detection signal derived from iron comprised in the oxygen scavenger composition, thereby distinguishing and detecting a metallic foreign material, and iron comprised in the oxygen scavenger, with respect to a magnetic substance, and thus simultaneously confirming the presence of the oxygen scavenger composition and inspecting the foreign material.

A known means (see, for example, JP 2005-345382 A) can be applied as a means for simultaneously detecting a magnetic substance and a non-magnetic substance, in the method of inspecting a product of the present invention.

EXAMPLES

Hereinafter, the present embodiment will be described in detail with reference to Examples and Comparative Examples, but the present embodiment can be appropriately modified as long as the effects of the present invention are exerted. Herein, "part(s)" in Examples and Comparative Examples means part(s) by mass, unless clearly noted particularly.

Example 1

(Production of Oxygen Scavenger Package)

1660 parts of diatomaceous earth (granular diatomaceous earth manufactured by Showa Chemical Industry Co., Ltd.), 1500 parts of activated carbon ("S-W50" manufactured by Futamura Chemical Co., Ltd., water content ratio 50% by mass), 300 parts of calcium bentonite ("Neo-Kunibond manufactured by Kunimine Industries Co., Ltd.) and 30 parts of sodium carboxymethyl cellulose ("F350HC-4" manufactured by Nippon Paper Industries Co., Ltd.) were loaded to a vertical granulator, and mixed for 30 seconds. Subsequently, an aqueous sodium chloride solution in which 545 parts of sodium chloride was dissolved in 2915 parts of water was loaded over 30 seconds, and furthermore mixed for 60 seconds, thereby obtaining a powdery/granular material (α layer).

Next, 8100 parts of an iron powder (manufactured by Hoeganaes AB, average particle size 90 μm) was load, subjected to purging of the vertical granulator with nitrogen, and thereafter subjected to mixing for 3 minutes, thereby obtaining a powdery/granular material (α layer/β layer) where the β layer was formed outside the powdery/granular material (α layer).

Furthermore, 120 parts of hydrophobic silica ("D17" Evonik Japan Co., Ltd.) was loaded under a nitrogen atmosphere, and mixed for 30 seconds, thereby obtaining an oxygen scavenger composition comprising a powdery/granular material (α layer/β layer/γ layer) where the γ layer was formed outside the powdery/granular material (α layer/β layer). The average particle size of the oxygen scavenger composition obtained was 0.9 mm.

A photograph of a cross section obtained by cutting the oxygen scavenger composition obtained, with a cutter, was taken with a digital microscope ("VHX-2000" manufactured by Keyence Corporation), and it was thus confirmed that the powdery/granular material (α layer/β layer/γ layer) had a structure having the α layer at the center portion, the β layer outside thereof and the γ layer further outside thereof.

The metallic iron content with respect to the iron powder used in production of the oxygen scavenger composition was measured according to the Bromine-Methanol dissolution EDTA titration method described in Commentary 5 of JIS M8213-1995 "Iron ores-Method for determination of acid soluble iron (II) content". As a result, the metallic iron content of iron used in production of the oxygen scavenger composition was 97.4% by mass.

Since purging with nitrogen was made in the step of production of the oxygen scavenger composition, a reduction in metallic iron content in iron due to oxidization almost did not occur. Thus, the metallic iron content of the oxygen scavenger composition was also 97.4% by mass.

0.8 g of the oxygen scavenger composition obtained was enclosed in a three-side sealed bag of 30 mm in length×40 mm in width, produced with an air permeable packaging material including a low-density polyethylene nonwoven fabric, thereby providing an oxygen scavenger package.

(Magnetism Detection Test)

The oxygen scavenger package obtained was enclosed in an oxygen barrier bag of 100 mm in length×100 mm in width, and sealed, thereby obtaining an oxygen scavenger sealed product. 3000 of such sealed products were produced, and such 3000 sealed products were subjected to a magnetism detection test with respect to iron and stainless steel by use of a metal detecting machine ("AD-4971-3517-E" manufactured by A & D Company, Limited).

First, an iron ball test piece having a diameter of 0.8 mm was used, and the transmit frequency at a sensitivity that enabled such an iron ball having a diameter of 0.8 mm or more to be detected as a foreign material was set in the metal detecting machine in advance. Five of such oxygen scavenger sealed products were randomly selected, an iron ball test piece having a diameter of 0.8 mm was enclosed in each of such oxygen scavenger sealed products, and such each oxygen scavenger sealed product enclosing the test piece was allowed to pass through the metal detecting machine, thereby measuring the detection voltage. The threshold of a sensitivity that enabled such an iron ball test piece having a diameter of 0.8 mm to be detected was set based on the detection voltage measured.

Next, 3000 of such oxygen scavenger sealed products (including no test piece) were each allowed to pass through the metal detecting machine and detection of a foreign material was performed. As a result of the measurement, all 3000 of such sealed products exhibited no abnormal detection, and exhibited the detection sensitivity of the iron ball having a diameter of less than 0.8 mm (less than the threshold).

The same measurement as described above was performed except that the test piece was changed to an iron ball having a diameter of 1.2 mm and the transmit frequency was accordingly changed. As a result of the measurement, all 3000 of such sealed products exhibited no abnormal detection.

Next, the same measurement as described above was performed except that the test piece was changed to a stainless ball having a diameter of 1.5 mm and the transmit frequency was accordingly changed. As a result of the measurement, all 3000 of such sealed products exhibited no abnormal detection, and exhibited the detection sensitivity of the stainless ball having a diameter of less than 1.5 mm (less than the threshold).

The same measurement as described above was performed except that the test piece was changed to a stainless ball having a diameter of 2.5 mm and the transmit frequency was accordingly changed. As a result of the measurement, all 3000 of such sealed products exhibited no abnormal detection.

As the respective diameters of the iron ball and the stainless ball were smaller, detection sensitivity was more excellent. In the food industry field, a detection sensitivity of an iron foreign material, of less than 0.8 mm, and a detection sensitivity of a stainless foreign material, of less than 1.5 mm, are acceptable.

3000 of such sealed products were each allowed to pass through the metal detecting machine at a decreased detection voltage, and iron derived from the oxygen scavenger was detected in all 3000 of such sealed products and enclosing of any oxygen scavenger package was detected.

(Measurement of Oxygen Absorption Time)

Such one oxygen scavenger package obtained and 250 mL of air was placed in a gas barrier bag of a nylon/polyethylene laminate film, and sealed. Storing was made at 25° C., and the time where the oxygen concentration in the gas barrier bag reached 0.1% or less was measured. The oxygen concentration was measured with a zirconia type oxygen concentration meter.

Comparative Example 1

An oxygen scavenger composition was obtained in the same manner as in Example 1 except that an iron powder having a metallic iron content of 89.8% by mass was used as an iron powder as a starting material.

Since purging with nitrogen was made in the step of production of the oxygen scavenger composition of Comparative Example 1, a reduction in metallic iron content in iron due to oxidization almost did not occur. Thus, the metallic iron content of the oxygen scavenger composition of Comparative Example 1 was also 89.8% by mass.

In a case where an iron ball having a diameter of 0.8 mm and a stainless ball having a diameter of 1.5 mm as test pieces were used for measurement, all 3000 of such oxygen scavenger packages each exhibited any detection sensitivity exceeding the detection sensitivities set as the respective thresholds of an iron ball having a diameter of 0.8 mm and a stainless ball having a diameter of 1.5 mm, and iron derived from the oxygen scavenger was wrong detected as a foreign material.

In a case where an iron ball having a diameter of 1.2 mm and a stainless ball having a diameter of 2.5 mm as test pieces were used for measurement, all 3000 of such oxygen scavenger packages exhibited no abnormal detection, and exhibited the detection sensitivity of the iron ball having a diameter of less than 1.2 mm (less than the threshold) and the detection sensitivity of the stainless ball having a diameter of less than 2.5 mm (less than the threshold). However, such sensitivities were insufficient detection sensitivities for combination use with metal inspection.

3000 of such sealed products were each allowed to pass through the metal detecting machine at a decreased detection voltage, and iron derived from the oxygen scavenger was detected in all 3000 of such oxygen scavenger packages and enclosing of any oxygen scavenger package was detected.

Comparative Example 2

The magnetism detection test and the measurement of the oxygen absorption time were performed in the same manner as in Example 1 except that the oxygen scavenger packages were each changed to "Ageless GLS-50" (glycerin-based oxygen scavenger manufactured by Mitsubishi Gas Chemical Company, Inc.).

In a case where an iron ball having a diameter of 0.8 mm and a stainless ball having a diameter of 1.5 mm as test pieces were used for measurement, no abnormal detection was observed, and the detection sensitivity of the iron ball having a diameter of less than 0.8 mm (less than the threshold) and the detection sensitivity of the stainless ball having a diameter of less than 1.5 mm (less than the threshold) were exhibited. The same measurement as described above was performed except that the respective test pieces were changed to an iron ball having a diameter of 1.2 mm and a stainless ball having a diameter of 2.5 mm and the transmit frequencies were accordingly changed. As a result of the measurement, all 3000 of such sealed products exhibited no abnormal detection.

3000 of such sealed products were each allowed to pass through the metal detecting machine at a decreased detection voltage, and enclosing of oxygen scavenger package was not detected because "Ageless GLS-50" comprised no iron.

Comparative Example 3

The magnetism detection test and the measurement of the oxygen absorption time were performed in the same manner as in Example 1 except that the oxygen scavenger packages were each changed to "Ageless GE-50" (erythorbic acid-based oxygen scavenger manufactured by Mitsubishi Gas Chemical Company, Inc.).

In a case where an iron ball having a diameter of 0.8 mm and a stainless ball having a diameter of 1.5 mm as test pieces were used for measurement, no abnormal detection was observed, and the detection sensitivity of the iron ball having a diameter of less than 0.8 mm (less than the threshold) and the detection sensitivity of the stainless ball having a diameter of less than 1.5 mm (less than the threshold) were exhibited. The same measurement as described above was performed except that the respective test pieces were changed to an iron ball having a diameter of 1.2 mm and a stainless ball having a diameter of 2.5 mm and the transmit frequencies were accordingly changed. As a result of the measurement, all 3000 of such sealed products exhibited no abnormal detection.

3000 of such sealed products were each allowed to pass through the metal detecting machine at a decreased detection voltage, and enclosing of oxygen scavenger package was not detected because "Ageless GE-50" comprised no iron.

TABLE 1

| | | Metallic iron content of iron (% by mass) | Magnetism detection test (number of detection) | | | | Detection of oxygen scavenger | Oxygen absorption time (day(s)) |
|---|---|---|---|---|---|---|---|---|
| | | | Detection of foreign material | | | | | |
| | | | Diameter of iron ball as test piece (*1) | | Diameter of stainless ball as test piece (*1) | | | |
| | Oxygen scavenger | | 0.8 mm | 1.2 mm | 1.5 mm | 2.5 mm | | |
| Example 1 | Composition (1) | 97.4 | 0 | 0 | 0 | 0 | 3000 | 0.5 |
| Comparative Example 1 | Composition (2) | 89.8 | 3000 | 0 | 3000 | 0 | 3000 | 0.5 |
| Comparative Example 2 | Glycerin-based | — | 0 | 0 | 0 | 0 | 0 | 1 |
| Comparative Example 3 | Erythorbic acid-base | — | 0 | 0 | 0 | 0 | 0 | 1 |

(*1) Diameter of test piece for use in setting of threshold of detection sensitivity The oxygen scavenger package of Comparative Example 1, using the iron-based oxygen scavenger, exhibited an insufficient detection sensitivity for combination use with metal inspection, although the presence of the oxygen scavenger package was confirmed by the metal detecting machine. Thus, it was difficult to detect a metallic foreign material after the oxygen scavenger was enclosed in a product such as a food or a pharmaceutical product.

Each of the oxygen scavenger packages of Comparative Examples 2 and 3, using the non-iron-based oxygen scavenger, did not comprise iron in the oxygen scavenger, and thus the presence of the oxygen scavenger package was not confirmed by use of the metal detecting machine. Such each oxygen scavenger package was long in oxygen absorption time and low in oxygen absorption performance, as compared with that in Example 1 where the iron-based oxygen scavenger was used.

On the contrary, the oxygen scavenger composition of Example 1 allowed the presence of the oxygen scavenger composition to be confirmed by use of the metal detecting machine, and an iron ball and a stainless ball were detected at high sensitivities.

INDUSTRIAL APPLICABILITY

The oxygen scavenger composition of the present invention can allow a metallic foreign material to be detected at a high sensitivity even after an iron-based oxygen scavenger composition is enclosed in a product such as a food or a pharmaceutical product, by inhibiting no detection of a metallic foreign material by a metal detecting machine and canceling a detection signal derived from the oxygen scavenger composition as a noise. Furthermore, a metal detecting machine provided with two or more frequency detectors can be used to perform detection, thereby simultaneously confirming the presence of the oxygen scavenger composition and detecting a metallic foreign material.

The invention claimed is:

1. A method of inspecting a foreign material in a product enclosing an oxygen scavenger composition comprising iron powder having a metallic iron content of 94% by mass or more by a metal detecting machine, the method comprising
a step of canceling a detection signal derived from the iron comprised in the oxygen scavenger composition as a noise,
wherein a detection principle of the metal detecting machine is according to a change in magnetic force.

2. The method according to claim 1, wherein the metallic iron content of the iron powder is 97% by mass or more and 99.5% by mass or less.

3. The method according to claim 1, wherein the metallic iron content of the iron powder is measured according to a Bromine-Methanol dissolution EDTA titration method.

4. The method according to claim 1, wherein the average particle size of the iron powder is 10 μm or more and 500 μm or less.

5. The method according to claim 1, wherein the iron powder is one kind or more selected from a group consisting of a reduced iron powder, an electrolytic iron powder or an atomized iron powder.

6. The method according to claim 1, wherein the oxygen scavenger composition comprises water, a water retention agent, a swelling agent and a metal salt.

7. A method of inspecting a product which is a product enclosing an oxygen scavenger composition comprising iron powder having a metallic iron content of 94% by mass or more by a metal detecting machine, the method comprising
performing detection by simultaneously using two or more frequency detectors to perform detection at a low frequency by one detector and perform detection at a high frequency by another detector, to simultaneously confirm the presence of the oxygen scavenger composition and inspect a foreign material.

8. The method according to claim 7, wherein simultaneously using two or more frequency detectors to thereby not only simultaneously detect a magnetic substance and a non-magnetic substance, but also specify a detection signal derived from the iron powder comprised in the oxygen scavenger composition, thereby distinguishing and detecting a metallic foreign material, and the iron powder comprised in the oxygen scavenger composition, with respect to a magnetic substance, to simultaneously confirm the presence of the oxygen scavenger composition and inspect a foreign material.

9. The method according to claim 7, wherein the metallic iron content of the iron powder is 97% by mass or more and 99.5% by mass or less.

10. The method according to claim 7, wherein the metallic iron content of the iron powder is measured according to a Bromine-Methanol dissolution EDTA titration method.

11. The method according to claim 7, wherein the average particle size of the iron powder is 10 μm or more and 500 μm or less.

12. The method according to claim 7, wherein the iron powder is one kind or more selected from a group consisting of a reduced iron powder, an electrolytic iron powder or an atomized iron powder.

13. The method according to claim 7, wherein the oxygen scavenger composition comprises water, a water retention agent, a swelling agent and a metal salt.

14. The method according to claim 13, wherein the metal salt is a metal halide.

15. The method according to claim 7, wherein the oxygen scavenger composition comprises a powdery/granular material having an α layer comprising a water retention agent, a swelling agent, a metal salt and water, a β layer comprising iron having a metallic iron content of 94% by mass or more, and a γ layer comprising a porous carrier,
wherein, in the powdery/granular material, a layered structure is formed including the α layer, the β layer and the γ layer in the listed order from an inside to an outside of the powdery/granular material.

16. The method according to claim 15, wherein the porous carrier is a silica compound.

17. The method according to claim 13, wherein the water retention agent comprises at least one selected from the group consisting of diatomaceous earth, silica and activated carbon.

18. The method according to claim 13, wherein the swelling agent comprises at least one selected from the group consisting of calcium carboxymethyl cellulose, sodium carboxymethyl cellulose, calcium bentonite and sodium bentonite.

19. The method according claim 15, wherein the powdery/granular material comprises 30% by mass or more and 50% by mass or less of the α layer, 49% by mass or more and 69% by mass or less of the β layer, and 0.1% by mass or more and 5.0% by mass or less of the γ layer, based on a total amount of the powdery/granular material.

20. The method according to claim 15, wherein the α layer comprises 1.0% by mass or more and 10% by mass or less of the swelling agent based on a total amount of the α layer.

* * * * *